(12) United States Patent
Wang et al.

(10) Patent No.: US 10,816,452 B2
(45) Date of Patent: Oct. 27, 2020

(54) EVALUATION METHOD FOR DIFFERENT TYPES OF PORE EVOLUTION IN SHALE

(71) Applicant: China University of Petroleum(East China), Qingdao, Shandong (CN)

(72) Inventors: Min Wang, Shandong (CN); Yang Liu, Shandong (CN); Chuanming Li, Shandong (CN); Shuangfang Lu, Shandong (CN)

(73) Assignee: China University of Petroleum(East China), Qingdao, Shandong (CN)

( * ) Notice: Subject to any disclaimer, the term of this patent is extended or adjusted under 35 U.S.C. 154(b) by 217 days.

(21) Appl. No.: 16/095,358

(22) PCT Filed: Jun. 15, 2017

(86) PCT No.: PCT/CN2017/088496
§ 371 (c)(1),
(2) Date: Oct. 20, 2018

(87) PCT Pub. No.: WO2018/218702
PCT Pub. Date: Dec. 6, 2018

(65) Prior Publication Data
US 2019/0331583 A1 Oct. 31, 2019

(30) Foreign Application Priority Data
Jun. 1, 2017 (CN) .......................... 2017 1 0404972

(51) Int. Cl.
*G01N 15/08* (2006.01)
*G01N 33/24* (2006.01)

(52) U.S. Cl.
CPC .......... *G01N 15/088* (2013.01); *G01N 33/24* (2013.01); *G01N 2015/0833* (2013.01)

(58) Field of Classification Search
CPC ............. G01N 15/088; G01N 15/0886; G01N 2015/0833; G01N 33/24
See application file for complete search history.

(56) References Cited

U.S. PATENT DOCUMENTS

2010/0154514 A1\* 6/2010 Algive ................... G01V 11/00
73/38
2012/0192639 A1\* 8/2012 Valenza, II ............. E21B 49/00
73/152.05

(Continued)

*Primary Examiner* — Francis C Gray (57) ABSTRACT

An evaluation method for different types of pore evolution in shale is related, which is applied to the field of unconventional oil and gas research. As the shale depth or maturity increases, different types of pores (including intergranular pores, intragranular pores, organic pores and fractures) developed in shale are constantly changing, which is important for shale oil and gas accumulation. The present invention starts from the high-resolution scanning electron micrography of shale, and respectively extracts the areal porosity of different types of pores based on the division criteria of different types of pores and pore identification in the established shale, and combines the low-temperature $N_2$, $CO_2$ adsorption experiments and the high-pressure mercury intrusion experiments to obtain the total pore volume and establish the evolution chart of different types of pores. The proposed method has an important application value for the exploration of unconventional shale oil and gas resources.

5 Claims, 8 Drawing Sheets

(56) References Cited

U.S. PATENT DOCUMENTS

| | | | |
|---|---|---|---|
| 2013/0013209 A1* | 1/2013 | Zhu | G01N 33/24 |
| | | | 702/6 |
| 2015/0166905 A1* | 6/2015 | Klein | B01J 23/883 |
| | | | 208/112 |
| 2017/0030819 A1* | 2/2017 | McCarty | C09K 8/605 |
| 2018/0003653 A1* | 1/2018 | Tinni | G01N 24/081 |
| 2018/0321416 A1* | 11/2018 | Freedman | G01V 3/32 |

* cited by examiner

EVALUATION METHOD FOR DIFFERENT TYPES OF PORE EVOLUTION IN SHALE

CROSS REFERENCE OF RELATED APPLICATION

This is a U.S. National Stage under 35 U.S.C 371 of the International Application PCT/CN2017/088496, filed Jun. 15, 2017, which claims priority under 35 U.S.C. 119(a-d) to CN 201710404972.0. filed Jun. 1, 2017.

BACKGROUND OF THE PRESENT INVENTION

Technical Field

The present invention relates to a method for exploring the unconventional oil and gas, and more specifically, to an evaluation method for different types of pore evolution in shale.

Description of Related Art

In conventional researches on the evolution of pores in shale, more attention is paid to organic pores. The main reason is that the content of methane adsorbed in the shale and the total gas (free gas and adsorbed gas) have a good positive correlation with the total organic carbon (TOC), indicating that the organic pores are probably the main space for the accumulation of shale gas (Chalmers and Bustin, 2008: Ross and Bustin, 2009; Zhang Linyi et al., 2009; Strapoć, 2010). A large number of organic pores are generally developed in the major gas-bearing shale in North America (Loucks et al., 2009; Ambrose et al., 2010; Curtis et al., 2011a; Slatt and O'Brien, 2011; Milliken et al., 2012). Organic pores have also been found in China's major lacustrine and marine shale (Zou Caineng et al., 2011; Liu Shugen et al., 2011; Chen Shangbin et al., 2012; Yao Suping, 2012; Tian et al., 2013; Yang Feng et al., 2013; Han Hui et al., 2013).

Previous research was mostly carried out on the evolution of the total pores of shale, including pores in organic matter and pores and fractures between or within other mineral particles. Katsube et al. (1992) studied the petrophysical characteristics of the shale from depth between 1000 meters and 4100 meters in the Beaufort-MacKenzie basin. The results showed that with the increase of buried depth, the degree of shale compaction increased, while the porosity decreased from 30% at 1000 meters to 5%~10% at 2500~4000 meters; the distribution of pore size gradually became unimodal, specifically the diameter of pores was mainly about 200 nm at 1000 meters, and with the increase of the depth, the diameter of the pore decreased to about 10~20 nm. Katsube (2000) believed that the connected porosity in shale decreased with the increasing pressure, but he only considered the effect of compaction on the pore structure, and did not consider the thermal evolution, cementation and dissolution. Mastalerz et al. (2013) studied the evolution characteristics of the pore structure of the New Albany shale, finding that the micropore volume, mesopore volume and macropore volume all showed a decrease and then an increase with the increase of thermal evolution. The phenomenon is explained by the fact that the formation of liquid hydrocarbons first occupies the pore space to reduce the pore volume, and then the liquid hydrocarbons are cracked into gas and discharged to release the pore space originally occupied by liquid hydrocarbons, thereby making the pore volume in each range of the pore diameter increase. Hu Haiyan (2013) studied the pore evolution characteristics of Woodford shale by simulation experiments. The results showed that the porosity and pore volume increased with the increase of thermal evolution, which, he believed, was caused by the thermal degradation of the organic matter. Cui Jingwei et al. (2013) carried out a high pressure thermal simulation experiment on low-matured Chang 7 shale of the Triassic Yanchang Formation of Ordos Basin, and obtained samples of different evolution stages and characterized their pore structure, finding that the volume of the large pore and the content of the residual hydrocarbon first increases and then decreases, and the micropore volume and mesopore volume show a decrease and then an increase with the increase of the simulated experimental temperature. Chen and Xiao (2014) obtained the shale samples with the degree of thermal evolution (Ro) from 0.69% to 4.19% by the thermal simulation experiments, and studied the change features of pore structure of these samples by the low-pressure gas adsorption. According to the experimental results, they divided the evolution of nano-pores in shale into three stages: formation stage (0.60%<Ro<2.0%), development stage (2.0%<Ro<3.5%) and transformation (destruction) stage (Ro>3.5%).

Most of the previous research is about the evolution of total pores, and there is no research on the evolution of different types of pores in shale. Mainly because of the complex pore evolution of shale, it is difficult to quantitatively characterize the porosity of different types of pores in different evolution stages. No identification basis and division principle are available for the different types of pores in shale. Although low-temperature $N_2$, $CO_2$ and high-pressure mercury intrusion experiments can quantitatively characterize the shale porosity at different evolution degrees, it is impossible to distinguish pore types. A high-resolution scanning electron microscope image can reflect the shape and size of pores, but there is no accurate concept available for identifying the pores of shale on the high-resolution scanning electron microscope image and no division principle available for dividing pores into different types. Conventionally, no reasonable and effective method is developed for evaluating the evolution of different types of pores in shale.

1. The present invention proposes and establishes an accurate concept for identifying the different types of pores in shale on a high-resolution scanning electron microscope image, and clarifies the division principle of different types of pores in shale. Therefore, it provides a practical method for the identification of different types of pores in shale for the broad mass of oil field researchers.

2. The present invention combines high-resolution scanning electron microscope images with the data of low-temperature $N_2$, $CO_2$ adsorption experiments and high-pressure mercury intrusion experiments, effectively solving the experimental problem that it is difficult to quantitatively characterize the porosity of shale using a high-resolution scanning electron microscope. The present invention also provides a feasible method for distinguishing different types of pores for the low-temperature $N_2$, $CO_2$ adsorption and high-pressure mercury intrusion experiments. A reasonable and effective method for evaluating different types of pores in shale is proposed.

3. The present invention is significant for analyzing the evolution of different types of pores in shale in a targeted area, and has an important application value for the exploration of unconventional shale oil and gas resources.

BRIEF SUMMARY OF THE PRESENT INVENTION

In view of the problems above, the present invention is to propose an evaluation method for different types of pore evolution in shale, and to establish the evolution chart of different types of pores in shale. The proposed method has an important application value for the exploration of unconventional shale oil and gas resources.

The technical solution of the present invention is as below: an evaluation method for different types of pore evolution in shale, specifically including the following steps of:

A) selecting shale samples: selecting a series of core samples with uniform organic matter types but different maturities or depths from a single basin/depression:

B) determining maturity, pyrolysis and total organic carbon of organic matter in shale: wherein a determination method should be in accordance with an industrial standard SY/T 5124-2012 Method of determining microscopically the reflectance of vitrinite in sedimentary rock, a Chinese national standard GB/T 18602-2012 Pyrolysis analysis of rocks, and a Chinese national standard GB/T 19145-2003 Determination of the total organic carbon in sedimentary rock:

C) acquiring a high-resolution scanning electron microscope image of shale: wherein samples are prepared, then polished, and finally viewed under a scanning electron microscope to acquire a high-resolution image;

D) establishing the division criteria of different types of pores: wherein according to a grayscale range of minerals/organic matter/pores, a contact relationship between the pores and the minerals, a pore development position and a pore morphology, the pores are divided into intergranular pores, intragranular pores, organic pores and fractures denoted by Inter, Intar. Org and Frac respectively; the pores in the high-resolution scanning electron microscope image are classified and marked according to the classification principle of the pores in a matrix of a shale reservoir;

E) acquiring the areal porosity of different types of the pores in shale: wherein first, the total pores in the scanning electron microscope image of shale are extracted by a threshold segmentation method, then the different types of the pores are accurately identified and marked according to the pore type division criteria established above and the image processing operation flow, and finally, the areal porosity of the different types of the pores are sequentially calculated, denoted by $SP_{1, Frac}$, $SP_{1, Org}$, $SP_{1, Intar}$, $SP_{1, Inter}$, ..., $SP_{n, Frac}$, $SP_{n, Org}$, $SP_{n, Intar}$, and $SP_{n, Inter}$ respectively. $SP_{1, Inter}$ represents the intergranular pore areal porosity of Sample 1, and n is a number of the shale samples;

F) determining a pore volume of the shale: wherein first, some samples are pulverized to 60 meshes, and the low-temperature $N_2$, $CO_2$ adsorption experiments are carried out, then 1 $cm^3$-sized block samples are selected to conduct high-pressure mercury intrusion experiments in accordance with GB/T 21650.1-2008 Determination of the pore size distribution and porosity of solid materials by mercury porosimetry and gas absorption, and finally, results of the three experiments are conjointly analyzed to obtain a total pore volume of the shale: V1, V2, ..., Vn. n is the number of the shale samples:

G) determining a volume of different types of the pores: wherein

Fracture volume $V_{i, Frac}$:

$$V_{i,Frac}=V_i \times PC_{i,Frac};$$

$$PC_{i,Frac}=SP_{i,Frac}/(SP_{i,Inter}+SP_{i,Intar}+SP_{i,Org}+SP_{i,Frac});$$

i=1, 2, ... m;
$V_i$ is the total pore volume of the $i^{th}$ sample;
$V_{i, Frac}$: the total volume of fractures;
$PC_{i, Frac}$ac: the pore contribution rate of fractures;
$SP_{i, Frac}$: the areal porosity of fractures;
Organic pore volume $V_{i, Org}$:

$$V_{i,Org}=V_i \times PC_{i,Org};$$

$$PC_{i,Org}=SP_{i,Org}/(SP_{i,Inter}+SP_{i,Intar}+SP_{i,Org}+SP_{i,Frac});$$

$V_i$ is the total pore volume of the $i^{th}$ sample;
i=1, 2, ... m;
$V_{i, Org}$: the total volume of organic pores;
$PC_{i, Org}$: the pore contribution rate of organic pores:
$SP_{i, Org}$: the areal porosity of organic pores:
Intragranular pore volume $V_{i, Intar}$:

$$V_{i,Intar}=V_i \times PC_{i,Intar};$$

$$PC_{i,Intar}=SP_{i,Intar}/(SP_{i,Inter}+SP_{i,Intar}+SP_{i,Org}+SP_{i,Frac});$$

$V_i$ is the total pore volume of the $i^{th}$ sample;
i=1, 2, ... m;
$V_{i, Intar}$: the total volume of intragranular pores;
$PC_{i, Intar}$: the pore contribution rate of intragranular pores;
$SP_{i, Intar}$: the areal porosity of intragranular pores;
Intergranular pore volume $V_{i, Inter}$:

$$V_{i,Inter}=V_i \times PC_{i,Inter};$$

$$PC_{i,Inter}=SP_{i,Inter}/(SP_{i,Inter}+SP_{i,Intar}+SP_{i,Org}+SP_{i,Frac});$$

$V_i$ is the total pore volume of the $i^{th}$ sample;
i=1, 2, ... m;
$V_{i, Inter}$: the total volume of intergranular pores;
$PC_{i, Inter}$: the pore contribution rate of intergranular pores:
$SP_{i, Inter}$: the areal porosity of intergranular pores:
m is the number of the shale samples; and H) establishing an evolution chart of the different types of the pores in the shale: wherein the evolution chart of the different types of the pores in the shale is established according to the volume and the maturity of these types of the pores in the shale;

furthermore, in the Step C) acquiring the high-resolution scanning electron microscope image of the shale: wherein the samples are prepared, polished, and viewed under the scanning electron microscope to acquire the image;

sample preparation: first, the shale sample is cut to prepare a test piece of about 1 cm×1 cm×1 cm (Length×Width×Height):

polishing: a surface of a vertical bedding is mechanically polished using a precision cutting and grinding machine (start from coarse sandpaper and polish it with 1000-mesh to about 20000-mesh sandpaper); a mechanically polished test piece is mounted rigidly with paraffin on a T-shaped sample holder made of aluminum; and the test piece is polished for 20 min at 5 KV 2 mA and then for 10 min at 2 KV 2 mA using an argon ion polisher (LEICA EM TIC 3X); and alternate operations are made for four times in total to complete the polishing of the surface of the test piece. In order to improve the energy utilization rate of argon ions, an angle between the polished surface and a direction of an argon ion beam is set to 3°.

FE-SEM observation: a MERLIN-type high-resolution field emission scanning electron microscop (FE-SEM) produced by ZEISS is used to image the polished surface of the test piece under low-voltage and low-current conditions of 1.2 KV~8 KV and 200 pA~80 pA.

Furthermore, in the Step D) establishing the division criteria of the different types of the pores:

the pores in the high-resolution scanning electron microscope image are classified according to the following classification principle of the pores in the matrix of the shale reservoir:

the high-resolution scanning electron microscope image of shale is an 8-bit chart with a grayscale range of 0-255 (black: 0, white: 255); graycale values of the minerals, the organic matter and the pores in the image are denoted by $G_{Min}$, $G_{Org}$ and $G_{Por}$.

Fracture: defined as a pore with a ratio of a major axis to a minor axis greater than 10. First, all the pores in the high-resolution scanning electron microscope image of the shale are extracted, then the ratio of the major axis to the minor axis is counted, and finally, the pores with the ratio of the major axis to the minor axis greater than 10 are marked as the fractures.

Organic pore: defined as a pore that develops inside and at the edge of organic matter. In a scanning electron microscope image, the organic matter is generally distributed in strips and has morphological characteristics. Its grayscale value is lower than that of the minerals and slightly higher than that of the pores. In a high-resolution scanning electron image, the grayscale range of the organic matter is $45\pm10 < G_{Org} < 100\pm10$ and the grayscale range of the pores is $0 \leq G_{Por} < 45\pm10$. First, distribution of the organic matter is extracted in the high-resolution scanning electron microscope image of the shale according to the grayscale range and morphological characteristics, then pores are extracted in a distribution range of organic matter, and finally, these pores are marked as the organic pores.

Intragranular pore: defined as a pore that develops inside a mineral particle. The intragranular pores mainly comprise: ① mold poles formed by way of partially or completely dissolving the particles: ② pores stored inside the fossil; ③ pores between crystals in a strawberry-like pyrite tuberculosis; ④ cleavage face (seam) pore in the clay and mica mineral particles; ⑤ internal pores of the particle (such as the inside of the pellet or fecal pellet). In the high-resolution scanning electron microscope image, the grayscale value of the minerals is larger than that of the organic matter, and has obvious external contour features. In the high-resolution scanning electron image, the mineral gray scale range is $105\pm5 < G_{Min} \leq 255$. In the high-resolution scanning electron microscope image of the shale, distribution of the mineral particles is first extracted according to the mineral gray scale range and the outer contour feature, then the pores are extracted in the mineral particles, and finally marked as the intragranular pores.

Intergranular pore: defined as a pore associated with mineral matrices that develop between particles and between crystals. The intergranular pore mainly comprises a quartz/feldspar/carbonate mineral intergranular pore, a quartz/feldspar particle edge pore and a feldspar cleavage pore. In the high-resolution scanning electron microscope image of the shale, all the pores are first extracted, then the fractures, the organic pores, and the intragranular pores are identified and eliminated, and finally remaining pores are marked as the intergranular pores.

Furthermore, in the Step E) acquiring of the areal porosity of the different types of the pores in the shale: wherein first, the total pores in the scanning electron microscope image of the shale are extracted by a threshold segmentation method, then the different types of the pores are accurately identified and marked according to the pore type division criteria established above and the image processing operation flow, and finally the areal porosity of the different types of the pores are sequentially calculated, denoted by $SP_{1, Frac}$, $SP_{1, Org}$, $SP_{1, Intar}$, $SP_{1, Inter}$, ..., $SP_{n, Frac}$, $SP_{n, Org}$, $SP_{n, Intar}$, and $SP_{n, Inter}$ respectively. $SP_{1, Inter}$ represents the intergranular pore areal porosity of Sample 1, and n is the number of the shale samples;

pore extraction: the total pores are extracted by a way of using difference in gray scales of different components of the scanning electron microscope image; a gray scale threshold of the image (the image is an 8-bit image with a grayscale range of 0-255) is adjusted, and the threshold is controlled to the extent that the pores in the image are all extracted; first, a Yen maximum correlation criterion is selected as the image threshold segmentation method, then the image is binarized, and finally the preliminary extracted pores are processed by a closed operation to improve accuracy of pore shape identification.

Pore classification extraction: according to the division criteria of different types of pores established and the image processing operation flow, the different types of the pores are accurately identified and marked, and the fractures, the organic pores, the intragranular pores and the intergranular pores are filled in black, 80% gray, 50% gray and 20% gray.

Extraction of the areal porosity: the classified pores are imported into Image J software, and the areal porosity of the different types of the pores is extracted according to difference in marking color, denoted by $SP_{1, Frac}$, $SP_{1, Org}$, $SP_{1, Intar}$, $SP_{1, Inter}$, ..., $SP_{n, Frac}$, $SP_{n, Org}$, $SP_{n, Intar}$, $SP_{n, Inter}$ and $SP_{1, Inter}$ respectively; n is the number of the shale samples.

The present invention has the following advantages due to the above technical solutions:

1. The present invention proposes and establishes an accurate concept for identifying different types of pores of shale on high-resolution scanning electron microscope images, and clarifies the division principle of different types of pores in shale. Therefore, it provides a practical method for the identification of different types of pores in shale for the broad mass of oil field researchers.

2. The present invention combines high-resolution scanning electron microscope images with the low-temperature N2, CO2 adsorption experiments and the high-pressure mercury intrusion experiments, effectively solving the experimental problem that the high-resolution scanning electron microscopy is difficult to quantify the porosity of shale. The present invention also provides a feasible method for distinguishing different types of pores for the low-temperature $N_2$, $CO_2$ adsorption and high-pressure mercury intrusion experiments. A reasonable and effective method for evaluating the evolution of different types of pores in shale is proposed.

3. The present invention is significant for analyzing the different types of pore evolution of shale in a targeted area, and has an important application value for the exploration of the unconventional shale oil and gas resources.

DETAILED DESCRIPTION OF THE PRESENT INVENTION

The technical solution of the present invention is further described through the embodiments in combination with the drawings as below.

Figure 1:
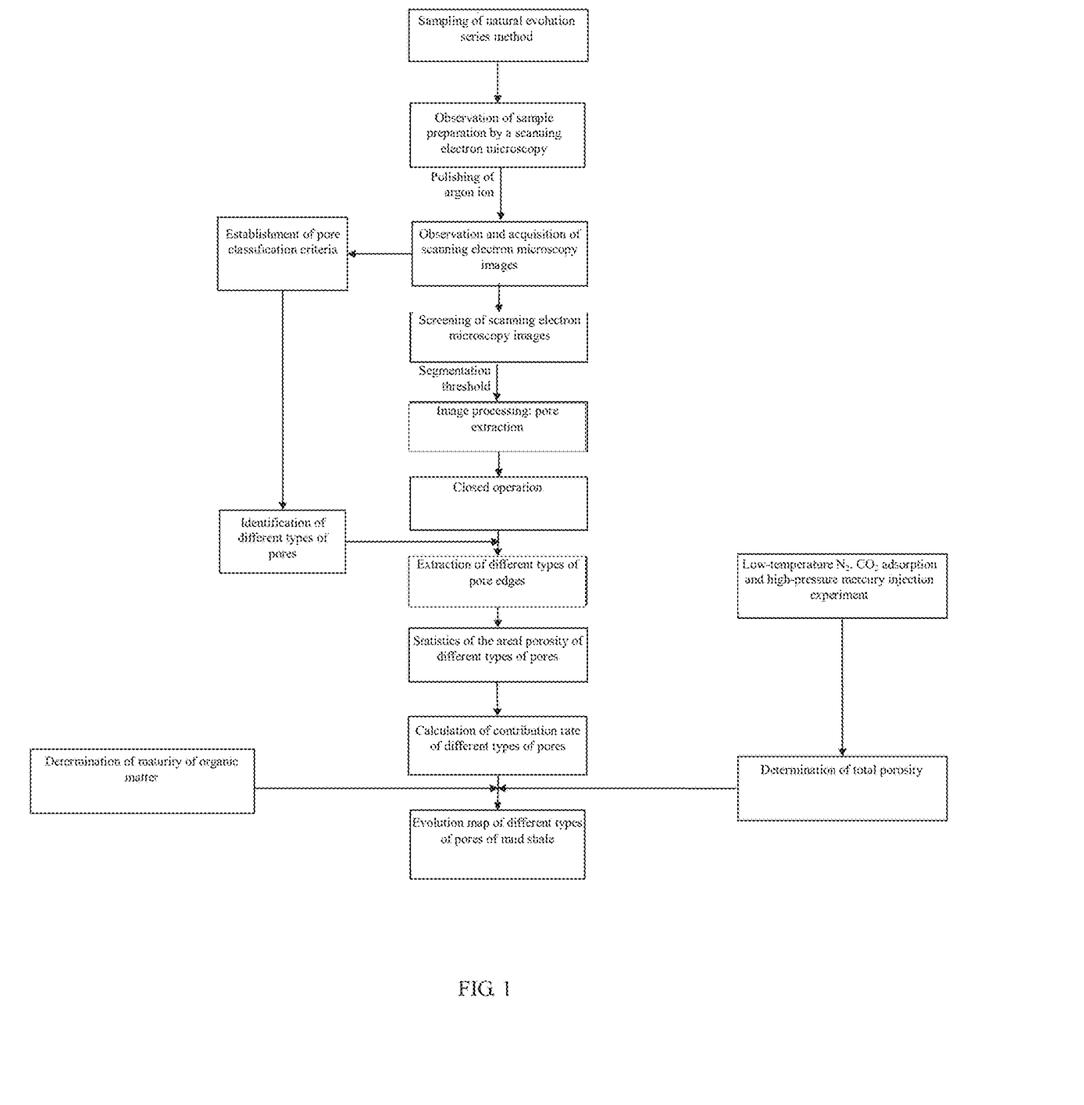
FIG. 1 is a flow chart of an evaluation method for different types of pore evolution in shale according to the present invention.

As shown in FIG. 1, an evaluation method for different types of pore evolution in shale in the present invention, specifically comprising the following steps of:

A) selecting shale samples: selecting a series of core samples with uniform organic matter types but different maturities or sample depths from a single basin/depression;

B) determining maturity, pyrolysis and total organic carbon of organic matter in shale: wherein a determination method should be in accordance with an industrial standard SY/T 5124-2012 Method of determining microscopically the reflectance of vitrinite in sedimentary rock, a Chinese national standard GB/T 18602-2012 Pyrolysis analysis of rocks, and a Chinese national standard GB/T 19145-2003 Determination of the total organic carbon in sedimentary rock:

C) acquiring a high-resolution scanning electron microscope image of shale: wherein samples are prepared, polished, and viewed under a scanning electron microscope to acquire an image;

D) establishing the division criteria of different types of pores: wherein according to a grayscale range of mineral/organic matter/pores, a contact relationship between the pores and the minerals, a pore development position and a pore morphology, the pores are divided into intergranular pores, intragranular pores, organic pores and fractures denoted by Inter, Intar. Org and Frac respectively: the pores in the high-resolution scanning electron microscope image are classified and marked according to the classification principle of the pores in a matrix of a shale reservoir;

E) acquiring the areal porosity of different types of the pores in shale: wherein first, the total pores in a shale scanning electron microscope image are extracted by a threshold segmentation method, then according to the pore type division criteria and image processing operation flow established above, different types of pores are accurately identified and marked, and finally the areal porosity of different types of pores are sequentially extracted, denoted by $SP_{1, Frac}$, $SP_{1, Org}$, $SP_{1, Intar}$, $SP_{1, Inter}$, ..., $SP_{n, Frac}$, $SP_{n, Org}$, $SP_{n, Intar}$, and $SP_{n, Inter}$ respectively. $SP_{1, Inter}$ represents the areal porosity of intergranular pores of Sample 1, and n is the number of shale samples;

F) determining a pore volume of the shale: wherein first, some samples are pulverized to 60 meshes, and the low-temperature $N_2$, $CO_2$ adsorption experiments are carried out, then 1 $cm^3$-sized block samples are selected to conduct high-pressure mercury intrusion experiments in accordance with GB/T 21650.1-2008 Determination of the pore size distribution and porosity of solid materials by mercury porosimetry and gas absorption, and finally, results of the three experiments are conjointly analyzed to obtain a total pore volume of the shale: V1, V2, ..., Vn. n is the number of the shale samples:

G) determining a volume of different types of the pores: wherein fracture volume $V_{i, Frac}$:

$$V_{i,Frac}=V_i \times PC_{i,Frac};$$

$$PC_{i,Frac}=SP_{i,Frac}/(SP_{i,Inter}+SP_{i,Intar}+SP_{i,Org}+SP_{i,Frac});$$

$V_i$ is the total pore volume of the $i^{th}$ sample;

i=1, 2, ... m;

$V_{i, Frac}$: the total volume of fractures;

$PC_{i, Frac}$: the pore contribution rate of fractures;

$SP_{i, Frac}$: the areal porosity of fractures;

Organic pore volume $V_{i, Org}$:

$$V_{i,Org}=V_i \times PC_{i,Org};$$

$$PC_{i,Org}=SP_{i,Org}/(SP_{i,Inter}+SP_{i,Intar}+SP_{i,Org}+SP_{i,Frac});$$

$V_i$ is the total pore volume of the $i^{th}$ sample;

i=1, 2, ... m;

$V_{i, Org}$: the total volume of organic pores;

$PC_{i, Org}$: the pore contribution rate of organic pores:

$SP_{i, Org}$: the areal porosity of organic pores:

Intragranular pore volume $V_{i, Intar}$:

$$V_{i,Intar}=V_i \times PC_{i,Intar};$$

$$PC_{i,Intar}=SP_{i,Intar}/(SP_{i,Inter}+SP_{i,Intar}+SP_{i,Org}+SP_{i,Frac});$$

$V_i$ is the total pore volume of the i sample;

i=1, 2, ... m;

$V_{i, Intar}$: the total volume of intragranular pores;

$PC_{i, Intar}$: the pore contribution rate of intragranular pores;

$SP_{i, Intar}$: the areal porosity of intragranular pores;

Intergranular pore volume $V_{i, Inter}$:

$$V_{i,Inter}=V_i \times PC_{i,Inter};$$

$$PC_{i,Inter}=SP_{i,Inter}/(SP_{i,Inter}+SP_{i,Intar}+SP_{i,Org}+SP_{i,Frac});$$

$V_i$ is the total pore volume of the $i^{th}$ sample;

i=1, 2, ... m;

$V_{i, Inter}$: the total volume of intergranular pores;

$PC_{i, Inter}$: the pore contribution rate of intergranular pores:

$SP_{i, Inter}$: the areal porosity of intergranular pores:

m is the number of shale samples;

H) establishing an evolution chart of the different types of the pores in the shale: wherein the evolution chart of the different types of the pores in the shale is established according to the volume and the maturity of these types of the pores in the shale;

2. An evaluation method for different types of pore evolution in shale as claimed in Claim 1, wherein furthermore, in the Step C) the acquiring the high-resolution scanning electron microscope image of the shale: wherein the samples are prepared, polished, and viewed under the scanning electron microscope to acquire the image;

sample preparation: first, the shale sample is cut to prepare a test piece of about 1 cm×1 cm×1 cm (Length× Width×Height);

polishing: a surface of a vertical bedding is mechanically polished by a precision cutting and grinding machine (start from coarse sandpaper and polish it with 1000-mesh to about 20000-mesh sandpaper); a mechanically polished sample is mounted rigidly with paraffin on a T-shaped sample holder made of aluminum; the test piece is polished for 20 min at 5 KV 2 mA and then for 10 min at 2 KV 2 mA using an argon ion polisher (LEICA EM TIC 3X); and alternate operations are made for four times in total to complete the polishing of the surface of the test piece. In order to improve the energy utilization rate of argon ions, an angle between the polished surface and a direction of an argon ion beam is set to 3°.

FE-SEM observation: a MERLIN-type high-resolution field emission scanning electron microscope produced by ZEISS is used to image the polished surface of the test piece under low-voltage and low-current conditions of 1.2 KV~0.8 KV and 200 pA~80 pA.

Furthermore, in the Step D), different types of pore division criteria are established:

the pores in the high-resolution scanning electron microscope image are classified according to the following classification principle of the pores in the matrix of the shale reservoir;

the high-resolution scanning electron microscope image of shale is an 8-bit chart with a grayscale range of 0-255 (black: 0, white: 255); graycale values of the minerals, the organic matter and the pores in the image are denoted by $G_{Min}$, $G_{Org}$ and $G_{Por}$.

Fracture: defined as a pore with a ratio of a major axis to a minor axis greater than 10. First, all the pores in the high-resolution scanning electron microscope image of the shale are extracted, then the ratio of the major axis to the minor axis is counted, and finally, the pores with the ratio of the major axis to the minor axis greater than 10 are marked as the fractures.

Organic pore: defined as a pore that develops inside and at the edge of organic matter. In a scanning electron microscope image, the organic matter is generally distributed in strips and has morphological characteristics. Its grayscale value is lower than that of the minerals and slightly higher than that of the pores. In a high-resolution scanning electron image, the grayscale range of the organic matter is $45\pm10 < G_{Org} < 100\pm10$ and the grayscale range of the pores is $0 \leq G_{Por} < 45\pm10$. First, distribution of the organic matter is extracted in the high-resolution scanning electron microscope image of the shale according to the grayscale range and morphological characteristics, then pores are extracted in a distribution range of organic matter, and finally, the pores are marked as the organic pores.

Intragranular pore: defined as a pore which develops inside a mineral particle. The intragranular pores mainly comprise: ① mold poles formed by way of partially or completely dissolving the particles: ② pores stored inside the fossil; ③ pores between crystals in a strawberry-like pyrite tuberculosis; ④ cleavage face (seam) pole in the clay and mica mineral particles: ⑤ internal pores of the particle (such as the inside of the pellet or fecal pellet). In the high-resolution scanning electron microscope image, the grayscale value of the minerals is larger than that of the organic matter, and has obvious external contour features. In the high-resolution scanning electron image, the mineral gray scale range is $105\pm5 < G_{min} \leq 255$. In the high-resolution scanning electron microscope image of the shale, distribution of the mineral particles is first extracted according to the mineral gray scale range and the outer contour feature, then the pores are extracted in the mineral particles, and finally marked as the intragranular pores.

Intergranular pore: defined as a pore associated with mineral matrices which develop between particles and between crystals. The intergranular pore mainly comprises a quartz/feldspar/carbonate mineral intergranular pore, a quartz/feldspar particle edge pore and a feldspar cleavage pore. In the high-resolution scanning electron microscope image of the shale, all the pores are first extracted, then the fractures, the organic pores, and the intragranular pores are identified and eliminated, and finally remaining pores are marked as the intergranular pores.

Furthermore, in the Step E) acquiring of the areal porosity of the different types of the pores in the shale: wherein first, the total pores in a shale scanning electron microscope image are extracted by a threshold segmentation method, then the total pores extracted are classified according to the classification criteria of pore types established above, and finally the areal porosity of different types of pores are sequentially extracted, denoted by $SP_{1,\ Inter}$, $SP_{1,\ Intar}$, $SP_{1,\ Org}$, $SP_{1,\ Frac}$, ..., $SP_{n,\ Inter}$, $SP_{n,\ Intar}$, $SP_{n,\ Org}$ and $SP_{n,\ Frac}$ respectively. $SP_{1,\ Inter}$ represents the areal porosity of intergranular pores of Sample 1, and n is the number of the shale samples:

pore extraction: the total pores are extracted by a way of using difference in gray scales of different components of the scanning electron microscope image; a gray scale threshold of the image (the image is an 8-bit image with a grayscale range of 0-255) is adjusted, and the threshold is controlled to the extent that the pores in the image are all extracted; first, a Yen maximum correlation criterion is selected as the image threshold segmentation method, then the image is binarized, and finally the preliminary extracted pores are processed by a closed operation to improve accuracy of pore shape identification.

Pore classification extraction: according to the division criteria of different types of pores established and the image processing operation flow, the different types of the pores are accurately identified and marked, and the fractures, the organic pores, the intragranular pores and the intergranular pores are filled in black, 80% gray, 50% gray and 20% gray.

Extraction of the areal porosity: the classified pores are imported into Image J software, and the areal porosity of the different types of the pores is extracted according to difference in marking color, denoted by $SP_{1,\ Frac}$, $SP_{1,\ Org}$, $SP_{1,\ Intar}$, $SP_{1,\ Inter}$, ..., $SP_{n,\ Frac}$, $SP_{n,\ Org}$, $SP_{n,\ Intar}$, $SP_{n,\ Inter}$ and $SP_{1,\ Inter}$ respectively; n is the number of the shale samples.

Embodiment 1

This sample is taken from the Qingshankou Formation of the Cretaceous in the Songliao Basin; taking the shale samples from the Jilin Oil field as an example, the evolution chart of different types of pores in shale of the Qingshankou Formation of the Cretaceous in the Jilin Oil field is established by way of using a method for evaluating the evolution of different types of pores. Specific steps are as follows:

A) Selecting shale samples: selecting a series of core samples with uniform organic matter types but different maturities or sample depths from a singlebasin/depression. Based on the research on different types of pore evolution in shale of the Qingshankou Formation of the Cretaceous in the Songliao Basin, the shale samples of the Chengshen 1, Xin 125, Cha 10, Cha 19, Rang 24 and Hei 62 wells are collected. The sample information (Table 1) is as follows:

TABLE 1

Basic information of samples

| Well name | Sample name | Depth (m) | Layer position | Sample description |
|---|---|---|---|---|
| Cheng shen 1 | JL1 | 666.8 | qn1 | Black-gray shale, with lamellation more developed and debris (pyrite, quartz) contained |
| Xin 125 | JL6 | 1265.9 | qn1 | Gray-black shale, with lamellation developed and a small amount of debris contained |
| Cha 19 | JL3 | 1586.8 | n1 | Gray-black shale, with lamellation more developed |
| Rang 24 | JL7 | 1868.4 | q4 | Gray shale, with lamellation not developed |
| Cha 10 | JL8 | 2000.2 | qn3 | Black-gray shale, with lamellation more developed and sandy layers contained |
| Cha 10 | JL2 | 2292.0 | q4 | Gray-black shale, with lamellation more developed and sandy layers contained |
| Hei 62 | JL4 | 2433.7 | qn1 | Gray-black shale, with fine sandy layers contained |

B) Determining maturity, pyrolysis and organic carbon of organic matter in shale: wherein the shale samples which reflect the entire targeted interval of the researching area are collected for routine experimentation (determination of maturity of organic matter, Rock-eval pyrolysis experiment, analysis test of the total organic carbon), and the experimental results (Table 2) are as follows:

TABLE 2

Experimental data of determination of maturity pyrolysis and organic carbon of organic matter in shale samples

| Sample name | Well name | Reflectivity (%) | S0 (mg/g) | S1 (mg/g) | S2 (mg/g) | $T_{max}$ (° C.) | TOC (%) |
|---|---|---|---|---|---|---|---|
| JL1 | Chengshen 1 | 0.55 | 0.02 | 0.68 | 34.81 | 441 | 4.96 |
| JL6 | Xin 125 | 0.58 | 0.01 | 1.51 | 15.98 | 442 | 2.63 |
| JL3 | Cha 19 | 0.64 | 0.03 | 2.77 | 40.89 | 442 | 5.85 |
| JL7 | Rang 24 | 1.35 | 0.01 | 0.09 | 0.2 | 460 | 0.49 |
| JL8 | Cha 10 | 1.03 | 0.01 | 0.14 | 0.83 | 442 | 0.52 |
| JL2 | Cha 10 | 1.08 | 0.02 | 0.58 | 0.68 | 450 | 1.12 |
| JL4 | Hei 62 | 1.26 | 0.02 | 0.17 | 0.47 | 449 | 0.66 |

Figure 2:
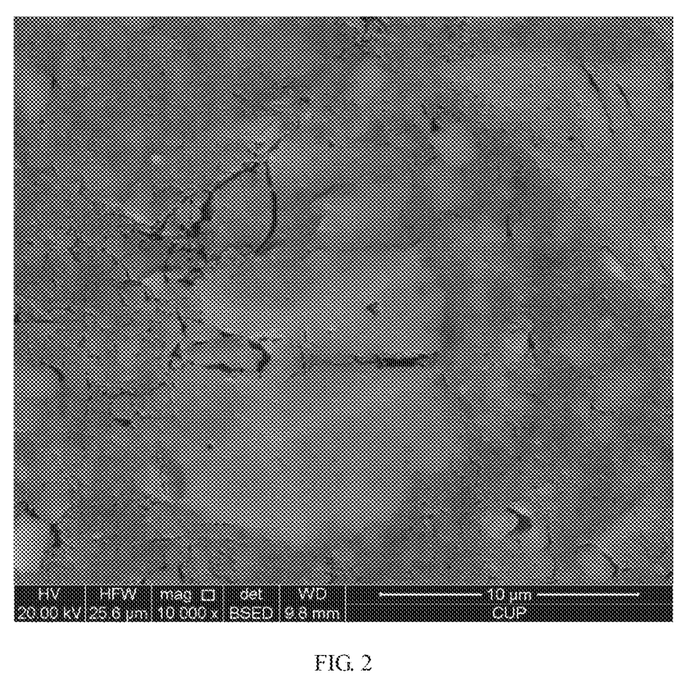
FIG. 2 is a high-resolution scanning electron micrograph of Sample JL1.
Figure 3:
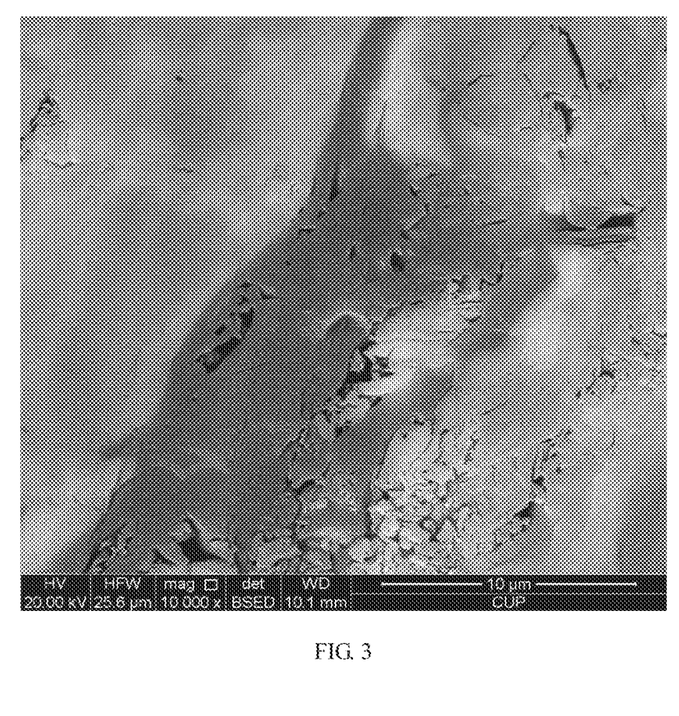
FIG. 3 is a high-resolution scanning electron micrograph of Sample JL6.
Figure 4:
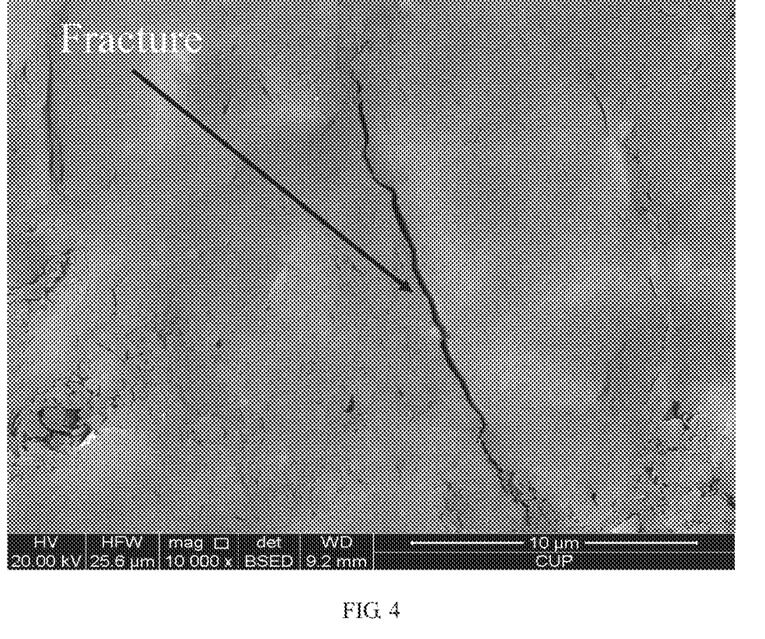
FIG. 4 is a template diagram of a fracture.
Figure 5:
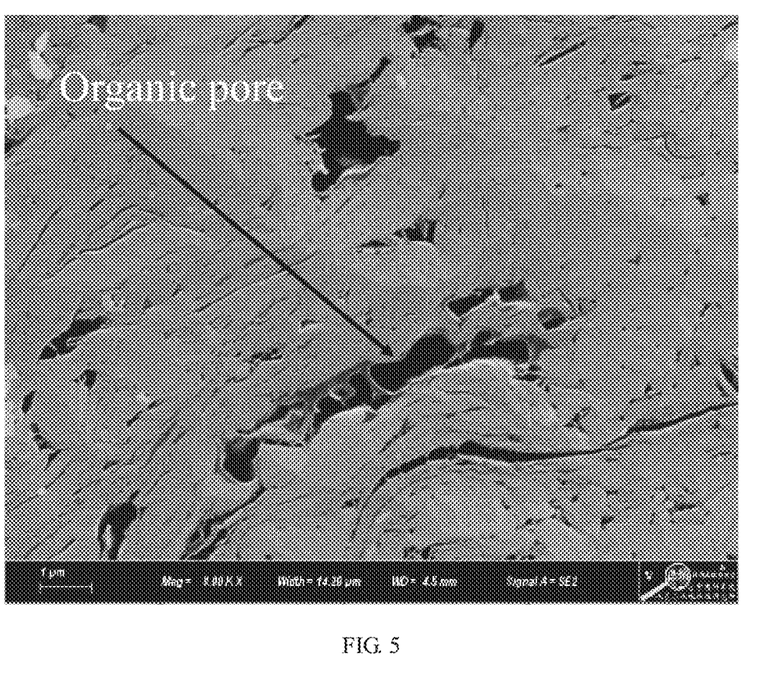
FIG. 5 is a template diagram of an organic pore.

C) Acquiring a high-resolution scanning electron microscope image of shale: wherein samples are prepared, polished, and viewed under a scanning electron microscope to acquire an image. This time, the samples from the Songliao Basin are selected; eight samples with maturity between 0.5% and 1.3% and with depths ranging from 666 m to 2432 m are taken for a high-resolution scanning electron microscopy; except for Sample SL5, a sandstone sample, the number of sampled shale samples for imaging processing are seven. Because the observation area of the scanning electron microscope image is relatively small and the shale is heterogeneous, in this research, 4 scanning electron microscope images of each sample are taken as an example and a total of 28 images are processed. High-resolution scanning electron microscope images of some samples (FIG. 2, FIG. 3).

D) Establishing different types of pore separation criteria: wherein according to the grayscale range of minerals/organic matter/pores, the contact relationship between pores and minerals, the pore development position and the pore morphology, pores are divided into intergranular pores, intragranular pores, organic pores and fractures, denoted by Inter, Intar, Org and Frac respectively; the pores in the high-resolution scanning electron microscope image are classified and marked according to the classification principle of pores in the matrix of the shale reservoir. Different types of pore templates are shown in the accompanying drawings (FIG. 4, FIG. 5, FIG. 6 and FIG. 7).

Figure 8:
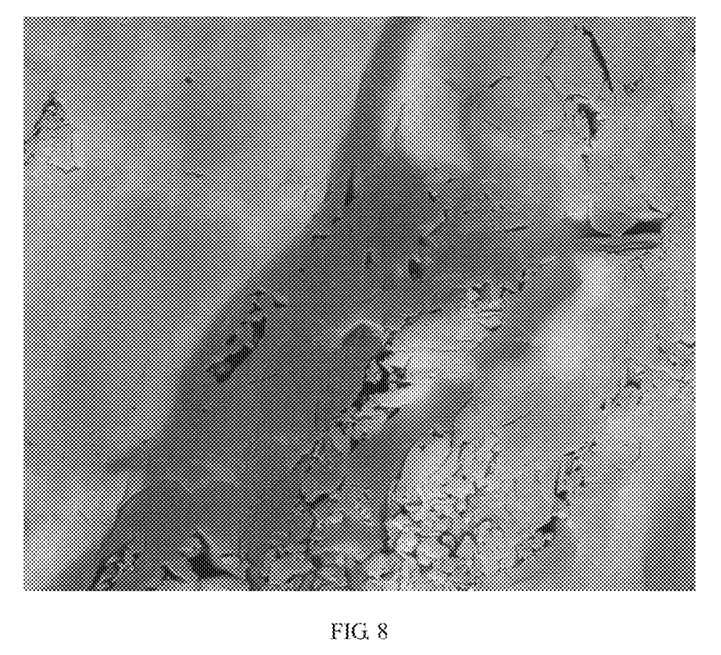
FIG. 8 is a cropped view of the JL6-03 high-resolution scanning electron microscope image.
Figure 9:
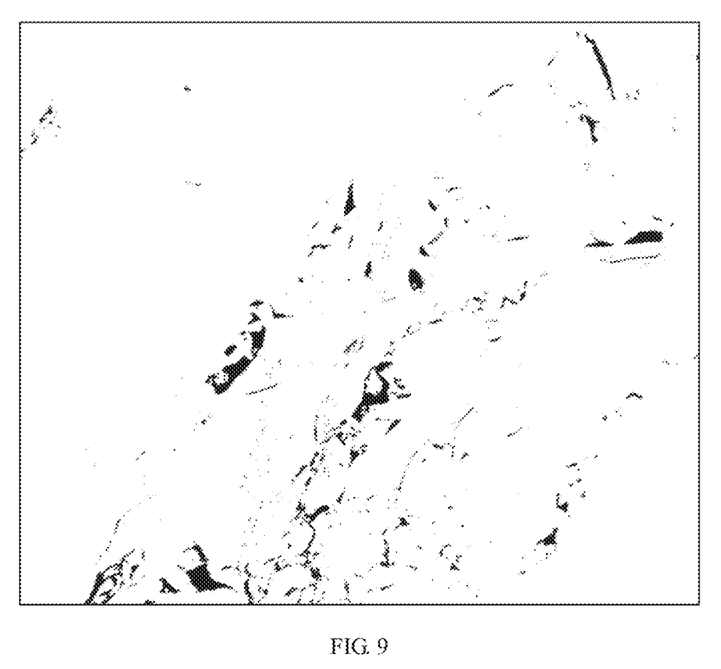
FIG. 9 is a diagram of the JL6-03 pore binarization process.
Figure 10:
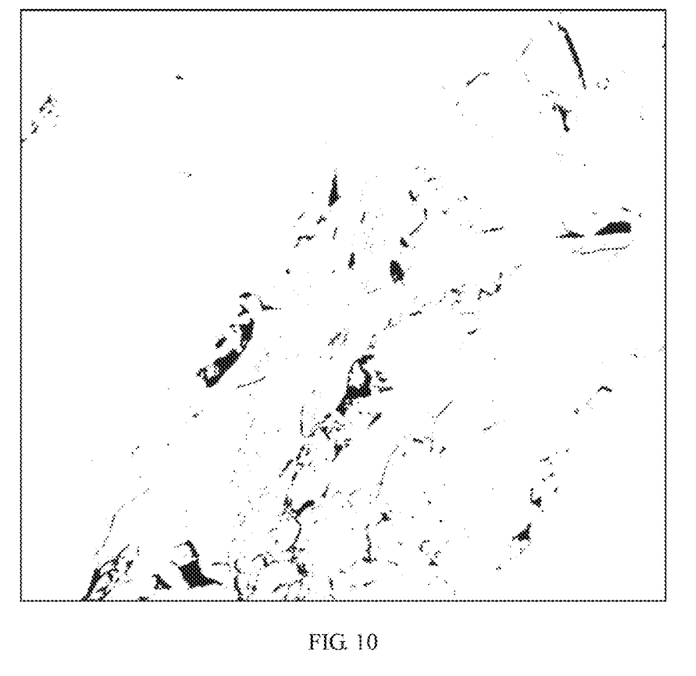
FIG. 10 is a diagram of the JL6-03 image closure operation processing.

E) Acquiring of the areal porosity of different types of pores in shale: wherein first, the total pores in the high resolution scanning electron microscope image of shale are extracted by a threshold segmentation method, then the total pores extracted are classified according to the pore type division criteria established above, and finally, the areal porosity of the different types of pores are sequentially calculated, denoted by $SP_{1, Frac}$, $SP_{1, Org}$, $SP_{1, Intar}$, $SP_{1, Inter}$, ..., $SP_{n, Frac}$, $SP_{n, Org}$, $SP_{n, Intar}$ and $SP_{n, Inter}$ respectively. $SP_{1, Inter}$ represents the intergranular pore areal porosity of Sample 1, and n is the number of shale samples;

Pore extraction: the high-resolution scanning electron microscope images of samples are clipped (FIG. 8). All the pores of JL6-03 are extracted by way of using the difference of gray scales of different components in the scanning electron microscope images, the gray scale threshold of the image (the image is an 8-bit image with a grayscale range of 0-255) is adjusted, and the threshold is controlled to the extent that the pores in the image are all extracted; first, the Yen maximum correlation criterion is selected as an image threshold segmentation method, then the image is binarized (FIG. 9), and finally the preliminary extracted pores are processed by a closed operation to improve the accuracy of pore shape identification (FIG. 10).

Figure 11:
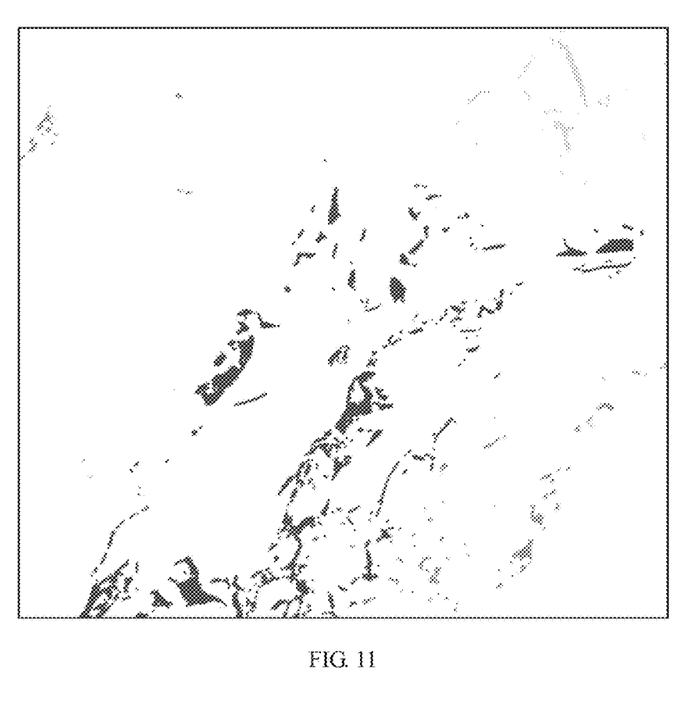
FIG. 11 is a distribution diagram of different types of the JL6-03 pores.

Pore classification extraction: according to the division criteria of different types of pores established in Claim 1 and the image processing operation flow, the different types of pores in the JL6-03 high-resolution scanning electron microscope image are accurately marked, and the organic pores, intragranular pores and intergranular pores are filled in 80% gray, 50% gray and 20% gray (FIG. 11).

Figure 12:
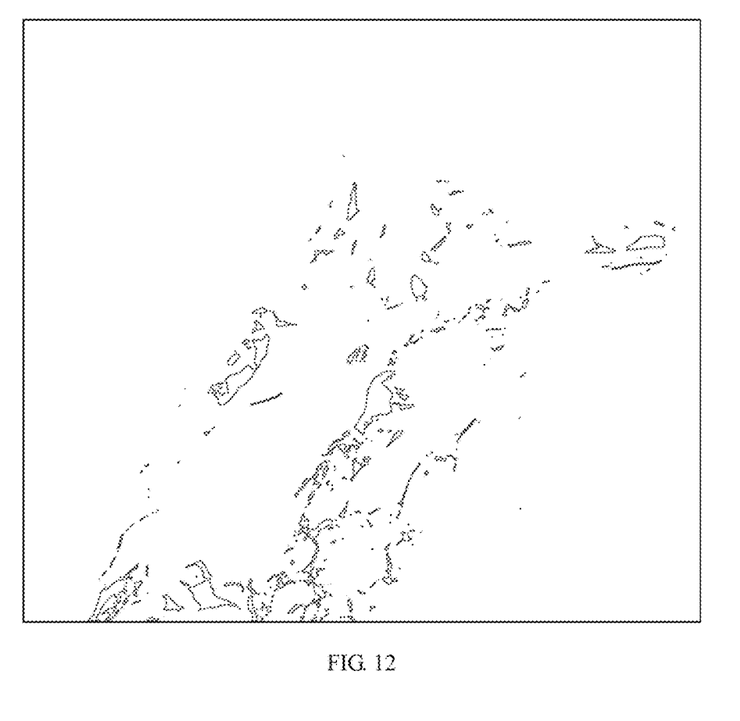
FIG. 12 is a distribution diagram of the pore profile of the JL6-03 organic pore.
Figure 13:
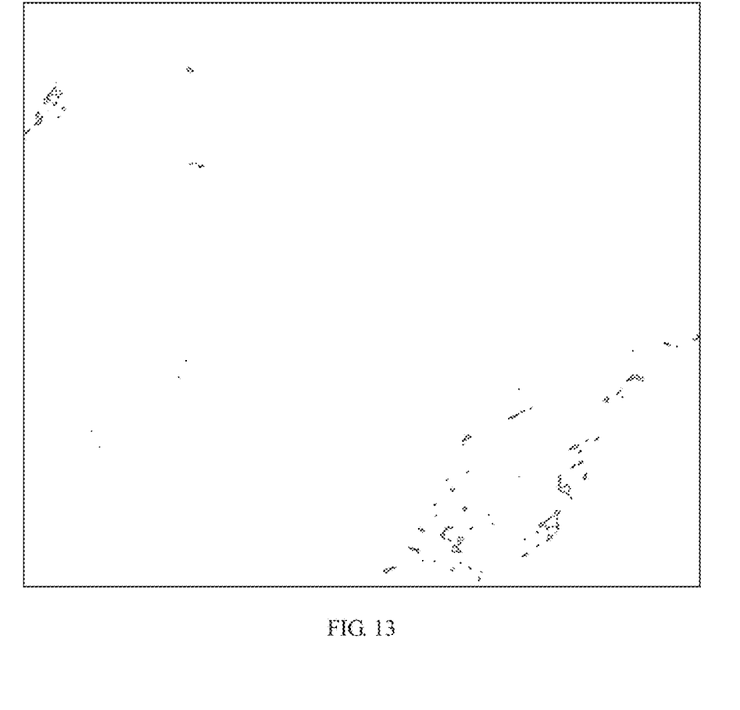
FIG. 13 is a distribution diagram of the pore profile of the JL6-03 intragranular pores.
Figure 14:
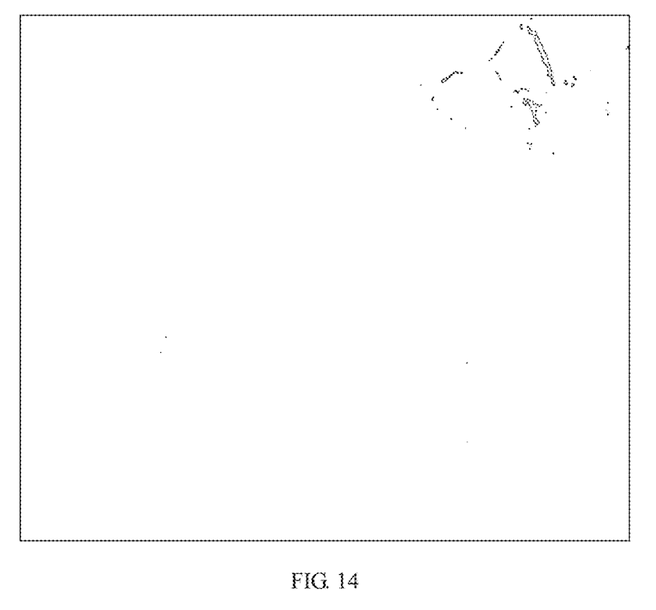
FIG. 14 is a distribution diagram of the pore profile of the JL6-03 intergranular pores.

Extraction of the areal porosity: the classified pores are imported into Image J software; different types of pore contours are extracted according to the difference of the marking colors (FIG. 12, FIG. 13 and FIG. 14) and the areal porosity of different types of pores are sequentially obtained (Table 3); after the four scanning electron microscope images of Sample JL6 are processed, the different pore face rates are summarized, and then the average areal porosity of different types of pores are calculated as $SP_{6,\,Org}$, $SP_{6,\,Intar}$, and $SP_{6,\,Inter}$. Finally, different pore contribution rates of $PC_{6,\,Org}$, $PC_{6,\,Intar}$, and $PC_{6,\,Inter}$ (Table 4) are calculated.

$$PC_{6,Inter}=SP_{6,Inter}/(SP_{6,Frac}+SP_{6,Org}+SP_{6,Intar}+SP_{6,Inter})$$

TABLE 3

Statistics of the areal porosity of different types of pores in JL6-03

| Pore types | Number of pores | Average areal porosity % |
|---|---|---|
| JL6_3 organic pores | 362 | 1.8276 |
| JL6_3 intragranular pores | 92 | 0.1759 |
| JL6_3 intergranular pores | 47 | 0.1391 |

TABLE 4

Average areal porosity and pore contribution rate of different types of pores in the JL6 sample

| Pore types of samples | Average areal porosity % | Pore contribution rate % |
|---|---|---|
| JL6 organic pores | 0.7217 | 34.0521 |
| JL6 intragranular pores | 0.0172 | 0.8116 |
| JL6 intergranular pores | 1.3805 | 65.1364 |

F) determining the pore volume of shale: wherein first, some samples are pulverized to 60 meshes, and the low-temperature $N_2$, $CO_2$ adsorption experiments are carried out, then 1 cm³-sized block samples are selected to conduct high-pressure mercury intrusion experiments in accordance with GB/T 21650.1-2008 Determination of the pore size distribution and porosity of solid materials by mercury porosimetry and gas absorption, and finally, the results of the three experiments are conjointly analyzed to obtain the total pore volume of shale: V1, V2, . . . . Vn. n is the number of shale samples.

TABLE 5

Data table of total pores of samples

| Sample name | Total porosity (%) |
|---|---|
| JL1 | 12.3466 |
| JL6 | 1.9897 |
| JL3 | 2.6349 |
| JL7 | 6.2328 |
| JL8 | 11.2577 |
| JL2 | 6.71948 |
| JL4 | 4.1254 |

Figure 6:
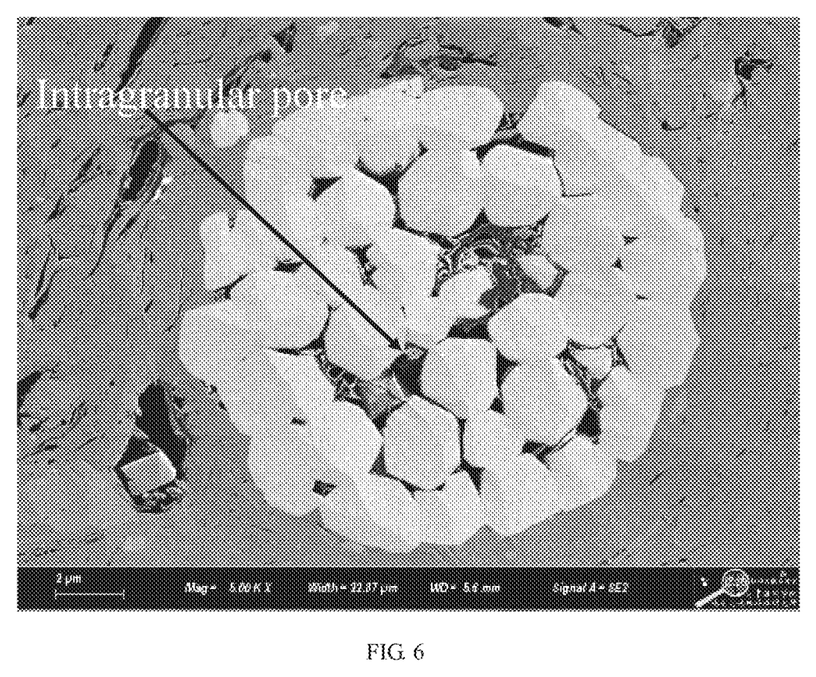
FIG. 6 is a template diagram of an intragranular pore.
Figure 7:
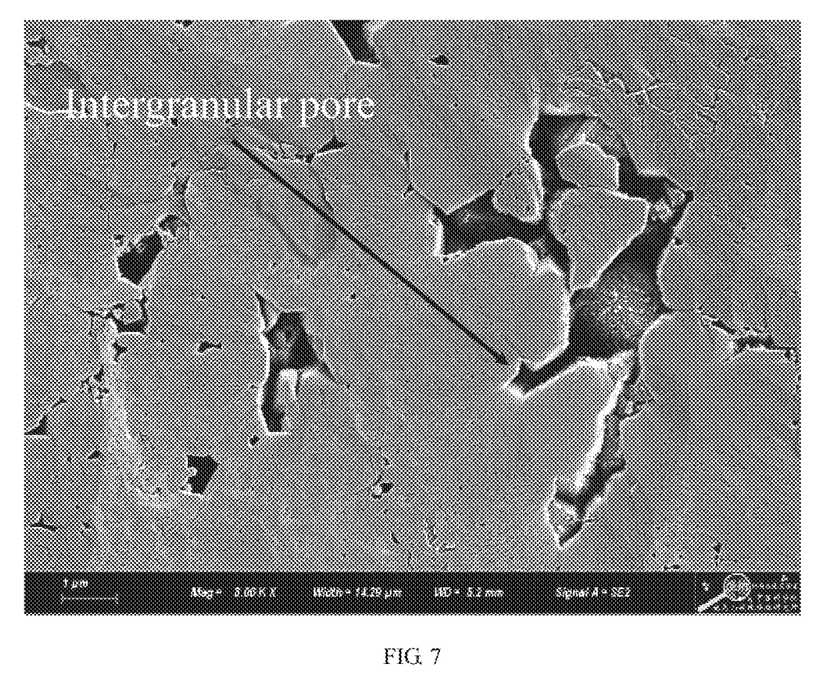
FIG. 7 is a template diagram of an intergranular pore.

G) determining the volume of different types of pores: wherein $V_{i,\,Frac}=V_i\times PC_{i,\,Frac}$; $V_{i,\,Org}=V_i PC_{i,\,Org}$; $V_{i,\,Intar}=V_i\times PC_{i,\,Intar}$; $V_{i,\,Inter}=V_i\times PC_{i,\,Inter}$; i=1, 2, . . . m; m is the number of shale samples;

FIG. 6 Volume of different types of pores of shale in the Qingshankou Formation of the Cretaceous in the Songliao Basin

| Sample name | Maturity | Porosity of fractures | Porosity of organic pores | Porosity of intragranular pores | Porosity of intergranular pores |
|---|---|---|---|---|---|
| JL1 | 0.55 | 0 | 2.0171 | 2.1778 | 12.3466 |
| JL6 | 0.58 | 0 | 0.6775 | 0.6937 | 1.9897 |
| JL3 | 0.64 | 0 | 0.6266 | 0.6677 | 2.6349 |
| JL8 | 1.03 | 0 | 1.3122 | 1.3895 | 11.2577 |
| JL2 | 1.08 | 0 | 0.5959 | 0.8958 | 6.7195 |
| JL4 | 1.26 | 0 | 0.3948 | 0.6203 | 4.1254 |
| JL7 | 1.35 | 0.2284 | 0.4899 | 3.3606 | 6.2328 |

Figure 15:
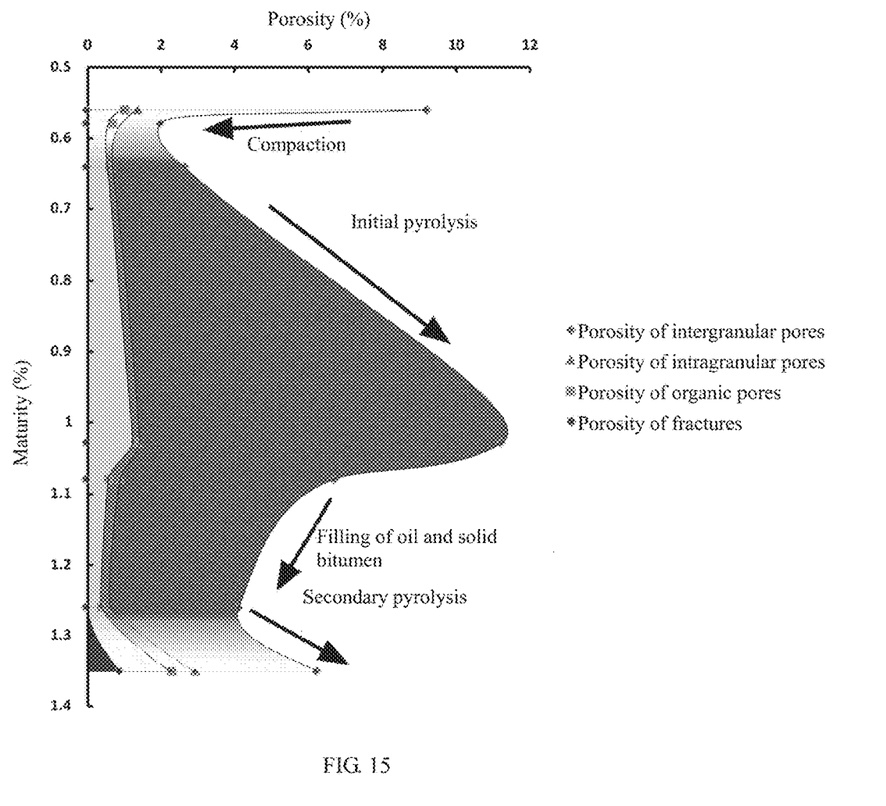
FIG. 15 is the evolution chart of different types of pores in shale in the Qingshankou Formation of the Cretaceous in the Songliao Basin.

H) Establishing the evolution chart of different types of pores in shale: wherein the evolution chart of different types of pores in shale is established according to the volume and maturity of these types of pores in shale (FIG. 15).

What is claimed is:
1. An evaluation method for different types of pore evolution in shale, wherein, specifically comprising the following steps of:
Step A) selecting shale samples: selecting a series of core samples with uniform organic matter types but different maturities or sample depths from a single basin/depression;
Step B) determining maturity, pyrolysis and total organic carbon of organic matter in shale: wherein a determination method is in accordance with an industrial standard SY/T 5124-2012 Method of determining microscopically the reflectance of vitrinite in sedimentary rock, a Chinese national standard GB/T 18602-2012 Pyrolysis analysis of rocks, and a Chinese national standard GB/T 19145-2003 Determination of the total organic carbon in sedimentary rock;
Step C) acquiring a high-resolution scanning electron microscope image of shale: wherein samples are prepared, polished, and viewed under a scanning electron microscope to acquire an image;
Step D) establishing different types of pore separation criteria: wherein pores in the high-resolution scanning electron microscope image are classified and marked according to a classification principle of the pores in a matrix of a shale reservoir;
Step E) acquiring an areal porosity of different types of the pores in shale: wherein first, the total pores in a shale scanning electron microscope image are extracted by a threshold segmentation method, then according to the pore type division criteria established above and image processing operation flow, the different types of the pores are accurately identified and marked, and finally the areal porosity of the different types of the pores are sequentially extracted;
Step F) determining a pore volume of the shale: wherein block samples are pretreated to conduct high-pressure mercury intrusion experiments in accordance with GB/T 21650.1-2008 Determination of the pore size distribution and porosity of solid materials by mercury porosimetry and gas absorption; finally, results of the three experiments are conjointly analyzed to obtain a total pore volume of the shale;
Step G) determining a volume of the different types of the pores: wherein each type of pore volume is calculated according to the total pore volume of the shale; and

Step H) establishing an evolution chart of the different types of the pores in the shale:
wherein according to the volume and the maturity of the different types of the pores in the shale, the evolution chart of the different types of the pores in the shale is established.

2. The evaluation method for the different types of the pore evolution in the shale as claimed in claim 1, wherein in the Step C) acquiring the high-resolution scanning electron microscope image of the shale: wherein the samples are prepared, polished, and viewed under the scanning electron microscope to acquire the image;
sample preparation: first, the shale sample is cut to prepare a test piece of about 1 cm×1 cm×1 cm (Length×Width×Height);
polishing: a surface of a vertical bedding is mechanically polished by a precision cutting and grinding machine; a mechanically polished sample is mounted rigidly with paraffin on a T-shaped sample holder made of aluminum; the test piece is polished for 20 min at 5 KV 2 mA and then for 10 min at 2 KV 2 mA using an argon ion polisher (LEICA EM TIC 3X); and alternate operations are made for four times in total to complete the polishing of the surface of the test piece; an angle between the polished surface and a direction of an argon ion beam is set to 3°;
FE-SEM observation: an MERLIN-type high-resolution field emission scanning electron microscope produced by ZEISS is used to image the polished surface of the test piece under low-voltage and low-current conditions of 1.2 KV~0.8 KV and 200 pA~80 pA.

3. The evaluation method for the different types of the pore evolution in the shale as claimed in claim 1, wherein in the Step D) establishing the division criteria of the different types of the pores:
establishment of the division criteria of the different types of the pores:
first, according to a gray range of minerals/organic matter/pores, a contact relationship between the pores and the minerals, a pore development position and a pore morphology, the pores are divided into intergranular pores, intragranular pores, organic pores and fractures, denoted by Inter, Intar, Org and Frac respectively; the pores in the high-resolution scanning electron microscope image are classified and marked according to the principle classification of the pores in the matrix of the shale reservoir;
then, the high-resolution scanning electron microscope image of the shale is an 8-bit chart with a grayscale range of 0-255 (black: 0, white: 255), and grayscale values of the minerals, the organic matter and the pores in the image are denoted by $G_{Min}$, $G_{Org}$ and $G_{Por}$;
finally, marking:
marking of the fractures: first, all the pores in the high-resolution scanning electron microscope image of the shale are extracted, then a ratio of a long axis to a short axis is counted, and finally, the pores with the ratio of the long axis to the short axis greater than 10 are marked as the fractures;
marking of the organic pores: first, distribution of the organic matter is extracted in the high-resolution scanning electron microscope image of the shale according to the gray scale range and morphological characteristics, that is, in a scanning electron microscope image, the organic matter is distributed in strips and has the morphological characteristics; its grayscale value is lower than that of the minerals and higher than that of the pores; the grayscale value of the organic matter is $45\pm10 < G_{Org} < 100\pm10$ and the grayscale value of the pores is $0 \leq G_{Por} < 45\pm10$, then the pores are extracted in a distribution range of the organic matter, and finally, these pores are marked as the organic pores Org;
marking of intragranular pores: first, distribution of mineral particles is extracted according to the grayscale range and external contour features of the minerals; in the high-resolution scanning electron microscope image, the minerals has a grayscale value larger than that of the organic matter, and has obvious external contour features, and the mineral grayscale range is $105\pm5 < GMin \leq 255$, then the pores are extracted in the mineral particles, and finally, these pores are marked as the intragranular pores;
marking of intergranular pores: first, all the pores are extracted in the high-resolution scanning electron microscope image of the shale, then the fractures, the organic pores, and the intragranular pores are identified and eliminated, and finally, remaining pores are marked as the intergranular pores.

4. The evaluation method for different types of pore evolution in shale as claimed in claim 1, wherein in the Step E) acquiring of the areal porosity of the different types of the pores in the shale: wherein first, the total pores in the scanning electron microscope image of the shale are extracted by the threshold segmentation method, then the different types of the pores are accurately identified and marked according to the pore type division criteria established above and the image processing operation flow, and finally, the areal porosity of the different types of the pores are sequentially calculated, denoted by $SP_{1,\ Frac}$, $SP_{1,\ Org}$, $SP_{1,\ Intar}$, $SP_{1,\ Inter}$, ..., $SP_{n,\ Frac}$, $SP_{n,\ Org}$, $SP_{n,\ Intar}$ and $SP_{n,\ Inter}$ respectively. $SP_{n,\ Inter}$ represents the intergranular pore areal porosity of Sample 1, and n is a number of the shale samples;
pore extraction: the total pores are extracted by a way of using difference of gray scales of different components in the scanning electron microscope image; a gray scale threshold of the image is adjusted to an 8-bit image with a grayscale range of 0-255; first, a Yen maximum correlation criterion is selected as the image threshold segmentation method, then the image is binarized, and finally the preliminary extracted pores are processed by a closed operation to improve accuracy of pore shape identification;
pore classification extraction: according to the division criteria of the different types of the pores established above and the image processing operation flow, the different types of the pores are accurately identified and marked, and fractures, organic pores, intragranular pores and intergranular pores are filled in black, 80% gray, 50% gray and 20% gray;
extraction of the areal porosity: the classified pores are imported into Image J software, and the areal porosity of the different types of the pores is extracted according to difference in marking color, denoted by $SP_{1,\ Frac}$, $SP_{1,\ Org}$, $SP_{1,\ Intar}$, $SP_{1,\ Inter}$, ..., $SP_{n,\ Frac}$, $SP_{n,\ Org}$, $SP_{n,\ Intar}$, $SP_{n,\ Inter}$ and $SP_{1,\ Inter}$ respectively; n is the number of the shale samples.

5. The evaluation method for different types of pore evolution in shale as claimed in claim 1, wherein a fracture volume $V_{i,\ Frac}$ is calculated according to an equation (1):

$$V_{i,Frac} = V_i \times PC_{i,Frac};$$

$$PC_{i,Frac} = SP_{i,Frac}/(SP_{i,Inter}+SP_{i,Intar}+SP_{i,Org}+SP_{i,Frac}); \quad (1)$$

wherein $PC_{i,Frac}$ is a pore contribution rate of fractures; $SP_{i,Frac}$ is an areal porosity of fractures; $V_i$ is a total pore volume of the $i^{th}$ sample; $i=1, 2, \ldots m$; m is a number of the shale samples;

an organic pore volume $V_{i,Org}$ is calculated according to an equation (2):

$$V_{i,Org}=V_i \times PC_{i,Org};$$

$$PC_{i,Org}=SP_{i,Org}/(SP_{i,Inter}+SP_{i,Intar}+SP_{i,Org}+SP_{i,Frac}); \quad (2)$$

wherein $PC_{i,Org}$ is a pore contribution rate of organic pores; $SP_{i,Org}$ is an areal porosity of organic pores; $V_i$ is a total pore volume of the $i^{th}$ sample; $i=1, 2, \ldots m$; m is the number of shale samples;

an intragranular pore porosity volume $V_{i,Intar}$ is calculated according to an equation (3):

$$V_{i,Intar}=V_i \times PC_{i,Intar};$$

$$PC_{i,Intar}=SP_{i,Intar}/(SP_{i,Inter}+SP_{i,Intar}+SP_{i,Org}+SP_{i,Frac}); \quad (3)$$

wherein $PC_{i,Intar}$ is a pore contribution rate of intragranular pores; $SP_{i,Intar}$ is an areal porosity of intragranular pores; $V_i$ is a total pore volume of the $i^{th}$ sample; $i=1, 2, \ldots m$; m is the number of shale samples;

an intergranular pore porosity volume $V_{i,Inter}$ is calculated according to an equation (4):

$$V_{i,Inter}=V_i \times PC_{i,Inter};$$

$$PC_{i,Inter}=SP_{i,Inter}/(SP_{i,Inter}+SP_{i,Intar}+SP_{i,Org}+SP_{i,Frac}); \quad (4)$$

wherein $PC_{i,Inter}$ is a pore contribution rate of intergranular pores; $SP_{i,Inter}$ is an areal porosity of intergranular pores; $V_i$ is a total pore volume of the $i^{th}$ sample; $i=1, 2, \ldots m$; m is the number of shale samples.

* * * * *